United States Patent
Thrier

(10) Patent No.: US 9,134,266 B2
(45) Date of Patent: Sep. 15, 2015

(54) REFERENCE ELECTRODE

(75) Inventor: Rolf Thrier, Tagelswangen (CH)

(73) Assignee: Mettler-Toledo AG, Greifensee (CH)

( * ) Notice: Subject to any disclaimer, the term of this patent is extended or adjusted under 35 U.S.C. 154(b) by 271 days.

(21) Appl. No.: 13/823,142

(22) PCT Filed: Dec. 15, 2011

(86) PCT No.: PCT/EP2011/072873
§ 371 (c)(1),
(2), (4) Date: Mar. 14, 2013

(87) PCT Pub. No.: WO2013/087106
PCT Pub. Date: Jun. 20, 2013

(65) Prior Publication Data
US 2014/0034515 A1    Feb. 6, 2014

(51) Int. Cl.
*G01N 27/30* (2006.01)
*G01N 27/403* (2006.01)
*F15D 1/00* (2006.01)
*G01N 27/411* (2006.01)
*G01N 27/416* (2006.01)

(52) U.S. Cl.
CPC ............. *G01N 27/301* (2013.01); *F15D 1/00* (2013.01); *G01N 27/302* (2013.01); *G01N 27/4035* (2013.01); *G01N 27/4117* (2013.01); *G01N 27/4166* (2013.01); *G01N 27/4167* (2013.01)

(58) Field of Classification Search
CPC .......... G01N 27/4166; G01N 27/4167; G01N 27/302; G01N 27/333; G01N 27/301; G01N 27/4117; G01N 27/4035
See application file for complete search history.

(56) References Cited

U.S. PATENT DOCUMENTS

| 3,686,091 | A |   | 8/1972 | Sawa |
| 4,264,424 | A | * | 4/1981 | Niedrach ................. 204/421 |
| 4,686,012 | A | * | 8/1987 | Engell et al. ............. 205/781.5 |
| 7,005,049 | B2 |   | 2/2006 | Broadley et al. |
| 7,089,994 | B2 |   | 8/2006 | Esposito et al. |
| 7,387,716 | B2 |   | 6/2008 | Ehrismann et al. |

(Continued)

FOREIGN PATENT DOCUMENTS

DE       3702501 A1    8/1987

OTHER PUBLICATIONS

Kenausis, Gregory L. et al., Poly(L-lysine)-g-Poly(ethylene glycol) Layers on Metal Oxide Surfaces: Attachment Mechanism and Effects of Polymer Architecture on Resistance to Protein Adsorption, J. Phys. Chem. B, 2000, pp. 3298-3309, 104(14).

(Continued)

*Primary Examiner* — Jennifer Dieterle
(74) *Attorney, Agent, or Firm* — Standley Law Group LLP

(57) ABSTRACT

A reference electrode with an in-situ modified porous diaphragm has at least one housing (1, 201, 301), a first conductor element (4, 204, 304), a modifying electrolyte which is capable of free-flow movement and is contained in the housing (1, 201, 301), and a porous diaphragm (3, 203, 303) which establishes a liquid connection between the modifying electrolyte and a measurement medium (9, 209, 309). The modifying electrolyte seeps out through the porous diaphragm during operation. The modifying electrolyte has a first component and a surface-modifying component which modifies the surface of the porous diaphragm (3, 203, 303) in situ during the passage of the modifying electrolyte. A method for modifying the porous diaphragm in situ is presented.

14 Claims, 6 Drawing Sheets

(56) References Cited

U.S. PATENT DOCUMENTS 7,790,323 B2 9/2010 Ehrismann et al.
2009/0166198 A1* 7/2009 Du et al. .................. 204/416

OTHER PUBLICATIONS

Basics of Potentiometry, Sep. 20, 2007, pp. 74-88.

* cited by examiner

REFERENCE ELECTRODE

TECHNICAL FIELD

The invention concerns a reference electrode for an electrochemical measuring chain with a porous diaphragm whose surface is modified in situ.

BACKGROUND OF THE ART

Reference electrodes are used in many electrochemical sensors and/or measuring chains, for example in potentiometric or amperometric sensors. These electrochemical sensors are employed in the laboratory as well as in various branches of industry such as the chemical industry, the food industry, the field of biotechnology, or the pharmaceutical industry. It is essential for electrodes of this kind that the reference potential which they provide be as constant as possible.

Reference electrodes of the known state of the art comprise for example a housing in whose interior an electrolyte is contained which, by way of an interface connection that is also referred to as liquid junction, is in contact with a measurement medium.

Further known among the prior art are reference electrodes which, in addition to the reference electrolyte, also comprise a bridge electrolyte, wherein the bridge electrolyte is in contact with a measurement medium by way of an liquid junction that is also referred to as liquid junction, and also has contact to the reference electrolyte by way of another interface. Dual-chamber systems of this kind are employed in particular if the reference electrolyte cannot be allowed to have direct contact to the measurement medium.

Particularly in the fields of biotechnology, pharmaceuticals, and in the food sector, stringent requirements are imposed on the reference electrode as well as the sensor as a whole and the materials contained inside it in regard to the absence of safety concerns and the ease of cleaning and sterilizing. The substances and materials that come into contact with the measurement medium should be chemically inert when exposed to the measurement medium and should preferably give no reason for concern; they should in particular not be toxic. The reference electrodes should be good to clean and sterilize. Known cleaning methods include for example CIP- and/or SIP-cycles (cleaning-in-place, sterilizing-in-place), which are performed under high temperature with strongly concentrated bases or acids. Furthermore, the so-called biofouling, i.e. deposits and accumulations of foreign or interfering substances occurring in particular on the diaphragm surface, should be prevented.

The liquid junction can for example consist of an open passage, or it may be configured as a porous diaphragm. The liquid junction should on the one hand have an electrical resistance as small as possible while on the other hand preventing the intermixing between the reference- or bridge electrolyte and the measurement medium. Attempts to meet this combination of requirements include a variety of measures.

For example in U.S. Pat. No. 7,387,716 B2 or EP 1 560 019, reference electrodes are disclosed which have an open interface passage in combination with solid or solidified reference electrolyte, for example a polymer electrolyte. In this way, an uncontrolled outflow of the reference electrolyte through the open interface passage can be prevented or at least strongly reduced. However, the polymer electrolytes that are being used for this consist in many cases of organic compounds which are not always harmless and which can even be toxic.

A further known attempt at a solution is to use porous diaphragms as liquid junctions, preferably in combination with a fluid electrolyte. The porous diaphragm likewise has the capability to prevent or at least strongly reduce the uncontrolled outflow of the reference- or bridge electrolyte through the liquid junction into the measurement medium. Porous diaphragms can be used for example in so-called pressurized reference electrodes of the kind disclosed for example in DE 3 702 501 A1. These reference electrodes are designed in such a way that the reference electrolyte, due to an internal overpressure, continuously seeps out of the pressurized reference electrode through the diaphragm. To prevent an overly rapid consumption of the reference electrolyte, the pores of the diaphragm should be as small as possible. By setting the reference electrolyte under pressure, a possible inflow of measurement medium as well as a clogging or blockage of the pores of the diaphragm can be prevented or at least mitigated by the outflowing reference electrolyte.

Nevertheless, reference electrodes with porous diaphragms still have drawbacks when used in biomass materials or protein-containing measurement media. A significant problem with the use of reference electrodes in protein-containing measurement media is the so-called biofouling. Most of the naturally occurring proteins, while having a neutral pH-value, carry a negative charge and therefore show an affinity towards adsorption on oxidic surfaces. Diaphragms often consist of oxidic substances such as for example oxidic ceramics, making them particularly prone to contamination and/or clogging in protein-containing measurement media, especially if diaphragms of a small pore size are used. The diaphragm contamination by protein-containing measurement media will falsify the interface potential and thereby cause measurement errors, wherein the tendency towards contamination gets stronger the smaller the pore size. The problems can even go as far as faulty measurement signals or a complete failure of the reference electrode. Even the raised internal pressure of a pressurized reference electrode and the resultant outward flow of the reference- or bridge electrolyte are not sufficiently effective to clean the diaphragm. Furthermore, it is possible for the measurement medium to become contaminated by the outflowing reference- or bridge electrolyte or by deposits on the diaphragm. However, it would be advantageous for the diaphragm to remain free of contamination during operation even when used in protein-containing measurement media or in biomass materials.

The known solutions that are used to avoid or reduce biofouling, specifically protein contamination of sensor surfaces and diaphragms, suffer from drawbacks. In pressurized reference electrodes, flushing of the porous diaphragm is possible only with a relatively high rate of outflow, which results in a high consumption of reference- or bridge electrolyte and thus frequent servicing of the electrodes to replenish the reference- or bridge electrolyte. With reference- or bridge electrolytes that are thickened and thus less free-flowing, cleaning of the diaphragm by flushing is not possible. In addition, many of the thickening agents that are used are organic substances which cannot be ranked as risk-free and which could for example contaminate the measurement medium. The reference- or bridge electrolyte can of course also be congealed with naturally occurring and essentially harmless polymers, such as for example agar-agar or cellulose. However, these substances will not stand up to the cleaning techniques mentioned above.

It is therefore the object of this invention to develop an improved reference electrode which delivers reliable and reproducible results even for measurements in biomass materials and, in addition, will hold up under the conventionally used cleaning procedures and process conditions.

SUMMARY

This task is solved by a reference electrode for electrochemical sensors which comprises a housing, a conductor element, a free-flowing modifying electrolyte contained in the housing, and a porous diaphragm. The porous diaphragm establishes a liquid connection or interface between the modifying electrolyte and measurement medium, wherein the modifying electrolyte seeps out through the diaphragm during operation. The modifying electrolyte comprises a first component and a surface-modifying component which modifies the surface of the diaphragm in situ during the passage of the modifying electrolyte.

The in-situ modification of the diaphragm surface is advantageous in comparison to a modification at the factory, because the modification can be performed in the operating state of the electrode, i.e. in situ, and an aging effect and/or a separation of the surface-modifying component, for example during CIP- and/or SIP-processes, can to a large extent be avoided, in contrast to a surface-modifying component that was applied before putting the electrode into service.

The diaphragm of the reference electrode consists of a porous material filled with pores that allow continuous passage through the diaphragm. The surface of the diaphragm in the present context therefore refers not only the surface facing towards the measurement medium, but also the surface presented by the pores.

The first component of the modifying electrolyte can be an electrolytically conductive and/or potential-defining substance of the kind that is used frequently, either as a component or by itself, for a reference electrolyte.

The first component is electrolytically conductive, the preferred choice being equitransferent salts whose anions and cations have essentially the same diffusion velocity in an aqueous solution. The use of equitransferent salts is advantageous as a way to reduce unwanted diffusion potentials at the interface.

In reference electrodes of the second kind, the first component can include a chloride compound such as for example KCl, NaCl, $MgCl_2$ or $CsCl_2$.

In dual-chamber reference system with bridge electrolyte as modifying electrolyte, the bridge electrolyte can include for example $Na_2SO_4$ as first component. Of course, other substances known as reference- or bridge electrolytes can also be used as first component of the modifying electrolyte. In pH-reference electrodes, the first component comprises a pH buffer system and in redox reference systems a redox buffer. The first component of the modifying electrolyte is used with preference in the form of aqueous solutions, particularly an aqueous potassium chloride solution, preferably in a concentration of 3 mol/L.

The in-situ modification of the porous diaphragm serves to prevent or at least strongly reduce biofouling on the surface of the porous diaphragm, as has already been attempted with a variety of measures.

Porous diaphragms can be coated for example with an inert polymer, for example PTFE (polytetrafluoroethylene) or a hydrophilic cross-linked hydrogel. Unfortunately, these coatings are difficult to apply, in some cases they easily detach themselves again and furthermore, they are relatively thick, so that the pores of the porous diaphragms are narrowed down too much, which can have the result of an undesirable increase in the flow resistance of the diaphragms.

As a further possibility, the diaphragm surface can be covered with substances that attach themselves through a covalent bond. However, this has the disadvantage, that the resultant covalent bonds are in many cases not resistant to hydrolysis, caused for example by the acids and bases that are used for cleaning, and that coatings of this kind detach themselves sometimes already after a single CIP treatment. The substances used for the coatings were for example silanes. In particular the PEGylation by means of silanes with a PEG (polyethylene glycol) radical, which almost completely inhibits the formation of protein deposits, still has the aforementioned disadvantages.

To overcome these drawbacks of the state of the art, the modifying electrolyte comprises besides the first component a surface-modifying component which, due to its characteristics, has the ability to modify the surface of the diaphragm in situ in such a way that the surface repels proteins and/or amino acids. The modification occurs in situ, which makes it possible to also use substances for the surface-modifying component which bond reversibly to the surface and thus alter the electric charge on the surface. Preferred are surface-modifying substances which, in addition, bond quickly with the surface. The surface-modifying component is added to the modifying electrolyte which seeps through the diaphragm during operation, so that during operation of the reference electrode the diaphragm surface retains a constant covering with the surface-modifying component, even if the substance being used for the surface-modifying component is reversibly adsorbent, or a substance which for example under the customary cleaning procedures detaches itself from the diaphragm surface.

In particular, the surface-modifying component that is being used should be non-toxic. This is especially important if the reference electrode according to the invention is to be used for measurements with biomasses or for protein-containing solutions.

The reference electrode is preferably designed for the continuous escape of the modifying electrolyte through the porous diaphragm during operation, so that the surface-modifying component can continuously modify the surface of the diaphragm.

This design of the reference electrode is particularly advantageous, as the continuous migration of the modifying electrolyte through the porous diaphragm has the result that the latter is on the one hand mechanically cleaned by the flow of modifying electrolyte which flushes foreign substances out of the porous diaphragm and on the other hand the surface modification can continuously be renewed or replenished. This is particularly advantageous if a kind of surface-modifying component is being used which reversibly bonds to the diaphragm surface or which bonds to the diaphragm surface through physisorption. A reversible bond can occur for example by way of hydrogen bridge bonds, electrostatic interaction, or Van-der-Waals forces.

As a means to ensure and preferably also to control the migration of the modifying electrolyte through the porous diaphragm, the reference electrode can be pressurized. Even with a non-pressurized reference electrode, diffusion and capillary forces would cause the surface-modifying component to spread slowly over the diaphragm surface or to be adsorbed to the diaphragm surface. As a result of the pressurization, the modifying electrolyte seeps through the diaphragm at a constant rate of outward flow, so that the modifying component is continuously sent through the pores of the diaphragm. This creates the conditions for an in-situ modification and in particular a continuous modification of the diaphragm surface. In addition, a relatively rapid in-situ modification can be achieved.

In one configuration of the reference electrode, the modifying electrolyte can be a reference electrolyte in which the conductor element is immersed.

In a further configuration of the reference electrode, the modifying electrolyte can be a bridge electrolyte which is in contact with the measurement medium by way of the diaphragm. The reference electrode in this configuration further comprises a reference electrolyte and a reference housing with a further diaphragm, wherein the conductor element is immersed in the bridge electrolyte and the reference electrolyte is in contact with the bridge electrolyte by way of the further diaphragm. Reference electrodes of this kind can for example comprise a dual-chamber system with an inner and an outer electrolyte, wherein the outer electrolyte, i.e. the bridge electrolyte, is in contact with the measurement medium by way of a diaphragm and comprises the surface-modifying component.

As an example of a further embodiment, a reference electrode according to the invention is configured as a pH electrode which comprises a pH buffer system as first component of the modifying electrolyte. Such systems are also referred to as differential pH measuring chains. The pH buffer system can comprise as first component a potential-defining substance, for example an acetate- or citrate buffer. For the surface-modifying component, one of the previously mentioned substances can be used.

Substances that can be used as surface-modifying component meet in particular the criterion that they are adsorbed at the diaphragm surface or settle on the diaphragm surface and subsequently inhibit the absorption of protein or the agglomeration of other or additional foreign substances. Preferably, the substance being used as surface-modifying component is non-toxic and chemically inert in relation to the measurement medium. The subsequent adsorption of foreign substances or interfering substances such as for example proteins can be inhibited either by electrostatically-acting or by sterically demanding substances.

Electrostatically-acting substances alter the surface charge of the diaphragm, whereby the adsorption of foreign substances at the surface of the diaphragm is inhibited so that biofouling is prevented or at least reduced. The adsorption at the diaphragm surface is enhanced or accelerated if attractive forces for the adsorbent, e.g. proteins, are predominant. The diaphragm surface that has been altered by an electrostatic substance possesses an electrostatic charge or electrostatic forces repulsive against adsorption, so that an unwanted protein adsorption on the diaphragm surface is electrostatically impeded. It should be noted here that the charge of the diaphragm as well as of the adsorbent is often a pH-dependent quantity.

In a further embodiment, a sterically demanding substance can be used as surface-modifying component which can sterically impede or even prevent the agglomeration of substances, particularly proteins that are contained in the measurement medium. The term "sterically demanding" refers to substances which, due to the amount of space occupied by them, can significantly impede the adsorption of further substances on the diaphragm surface. The same phenomenon can also affect the kinetics of reactions and for example slow down competing adsorptions, as the adsorption of further substances can be impeded by the previously adsorbed space-occupying substance. An example of a sterically demanding substance is polyethylene glycol (PEG).

In further embodiments, the surface-modifying component can be an organic substance which comprises at least one hydroxy substituent and at least one carbonyl substituent. These substances can bond to the diaphragm surface through hydrogen bridge bonds, among others, and thus impede the adsorption of further substances such as for example proteins.

Examples of organic substances of this kind are organic acids such as lactic acid, citric acid, malic acid, tartaric acid, ascorbic acid as well as their salts, or mixtures thereof. All of these compounds include at least one hydroxyl- and one carbonyl substituent and are furthermore distinguished by the fact that they are non-toxic. The dicarboxylic acids which have been mentioned as examples are negatively charged, which makes them particularly effective in attaching themselves to positively charged diaphragm surfaces through adsorption.

Malic acid, ascorbic acid or other reducing agents are used preferably in reference electrodes with a modifying electrolyte that is free of silver chloride, because especially at higher temperatures, these substances could cause an unwanted reduction of the silver chloride into silver.

Surprisingly, it has been found that especially citric acid and its salts, due to their reduction potential, cause essentially no change in reference electrodes with an AgCl-containing modifying electrolyte even at elevated temperatures. Consequently, citric acid and its salts are particularly well suited for use as surface-modifying component in Ag/AgCl reference electrodes.

A further embodiment of the reference electrode can include polylysine polyethylene glycol (pLy-PEG) as surface-modifying component. This substance, by means of its polyamino acid portion, can be adsorbed by an oxidic surface, whereupon the PEG portion that faces away from the surface can prevent the adsorption of further unwanted foreign substances or interfering substances. The term "foreign substances" in this context refers for example to proteins and other molecules out of a biomass that are prone to adsorption or agglomeration on an open diaphragm surface and would therefore clog up the diaphragm and make it unusable.

Preferably, the surface-modifying component is added to the modifying electrolyte in a low concentration of less than 0.1 percent by weight (wt %) and in particular from about 0.01 to 0.1 wt %. This concentration is sufficient to ensure a modification of the diaphragm surface and at the same time low enough that the occurrence of interfering diffusion potentials due to the added surface-modifying component is essentially prevented or at least strongly reduced.

The porous diaphragm can be for example a ceramic material or can include a metallic structure with a large surface.

It is preferred to use zirconium-containing ceramics as they withstand bases particularly well and are also stable under the conventional cleaning procedures, which makes them particularly suitable for use as porous diaphragms in reference electrodes.

As a further possibility, aluminum silicate ceramics can be used as porous diaphragms, but they are significantly less resistant to the conventional cleaning methods.

An example of a metallic structure has the form of a bundle of capillaries or a clump of metal wires consisting for example of a precious metal and in particular of passivated platinum.

The aforementioned ceramic materials as well as the metallic structures are distinguished by their high tolerance to the normally encountered process conditions and cleaning methods.

A further aspect of the invention concerns a method for the in-situ modification of a porous diaphragm which is arranged as interface or liquid passage in a reference electrode according to the invention. This method comprises among other features the step of adding a surface-modifying component to a modifying electrolyte that is contained in the reference electrode as well as ensuring the outward migration of the modifying electrolyte through the porous diaphragm. In this way, the surface of the diaphragm of a reference electrode can be modified during operation, i.e. in situ, and a blockage and/or contamination of the diaphragm by other substances which are present for example in the measurement medium can be effectively prevented.

In an advantageous embodiment, the reference electrode is pressurized in order to ensure a continuous flow of the modified electrolyte through the diaphragm.

A variety of exemplary embodiments a reference electrode in accordance with the invention as well as the method for in-situ modification of a porous diaphragm will be explained in the following with the help of the drawings wherein features that are identical from one figure to another are identified by the same reference symbols. The embodiments are described in particular through the example of a pH measuring chain with a reference electrode according to the invention which includes a reference electrolyte. In the following, the term "reference electrolyte" is therefore used in part synonymously with the term "modifying electrolyte". A reference electrode according to the invention can of course also be used with other electrochemical measuring chains or sensors.

DETAILED DESCRIPTION

Figure 1:
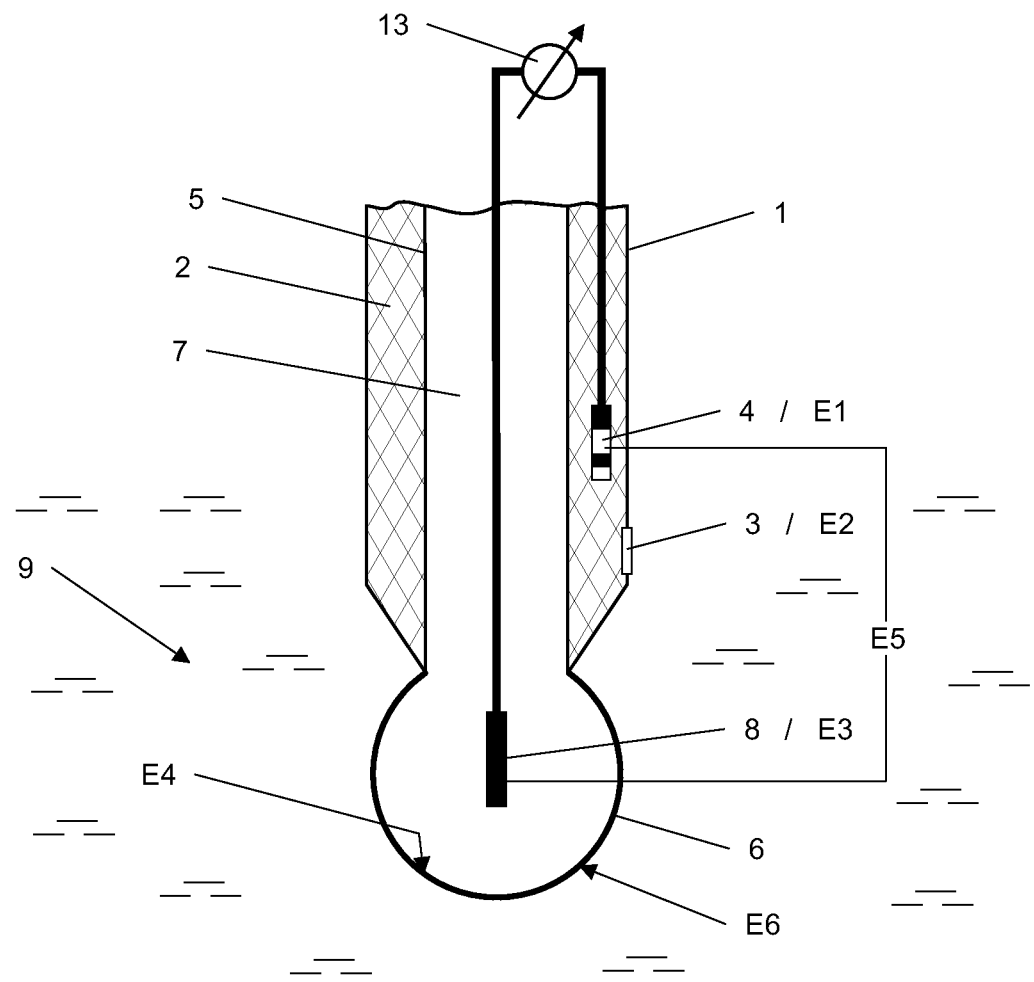
FIG. 1 schematically represents a combined pH measuring chain with a reference electrode in lengthwise sectional view.

FIG. 1 schematically illustrates a combined pH measuring chain with a pressurized reference electrode in sectional view. The reference electrode has an essentially tubular-shaped housing 1 which is filled with a reference electrolyte 2. A passage in the wall of the reference electrode is configured as a porous diaphragm 3 through which the reference electrolyte 2 escapes in a continuous flow during operation. A first reference element or conductor element 4 is immersed in the reference electrolyte 2.

The pH measuring chain further consists of an interior housing 5 which is arranged inside the housing 1, comprises a pH-sensitive glass membrane 6, and is filled with an inner buffer 7. Immersed in the inner buffer 7 is a second conductor element 8.

For the pH measurement, the pH measuring chain is immersed in a measurement medium 9, so that at least the glass membrane 6 and the porous diaphragm 3 are in contact with the measurement medium. The reference electrolyte 2 is in contact with the measurement medium 9 by way of the diaphragm 3.

One of the best-known reference electrodes for pH measuring chains is the so-called Ag/AgCl electrode with a first conductor element 4 of Ag/AgCl and a chloride-containing first component of the reference electrolyte 2, for example a KCl solution. Other state-of-the-art reference electrodes are AgCl-free pH-differential electrodes or redox reference electrodes.

According to the invention, a surface-modifying component is added to the reference electrolyte 2. The latter consists in essence of a first component, so that the reference electrolyte 2 with the addition of the surface-modifying component is the modifying electrolyte in accordance with the invention. In reference electrodes or reference systems containing silver ions, the surface-modifying component that is added to the reference electrolyte 2 is preferably of a kind that does not have a reducing effect even at a temperature around or above 130° C., such as for example citric acid and its salts. The surface-modifying component that is added to the modifying electrolyte of a pH-differential electrode is preferably of a kind which by itself constitutes a buffer system, such as for example a citrate buffer.

The state of the art includes many other types of reference electrodes for use in electrochemical sensors which are not described in detail here. Of course, all of these further types of reference electrodes can likewise be modified in the sense of the invention by adding a suitable surface-modifying component to the modifying electrolyte.

Further in FIG. 1, the electrochemical potentials are indicated which occur during a measurement in a pH measuring chain and which can influence the measurement result. Among these are the potential E1 of the first conductor element 4, the diffusion potential or the diaphragm potential E2 across the diaphragm 3, the potential E3 of the second conductor element, the potential E4 on the inside of the glass membrane 6, the asymmetry potential E5 between the first and the second conductor element 4, 8, and the pH-dependent potential E6 on the outside of the glass membrane 6.

The potential occurring between the two conductor elements 4, 8, in this example the pH potential E5, can be measured with a voltmeter 13 and is composed of the sum of the indicated potentials. It can be converted into a pH-value. In a state-of-the-art Ag/AgCl reference electrode, the potential E1 according to the Nernst equation corresponds to the potential of the chlorine ions at the first conductor 4. The potential E1 is essentially constant as long as the concentration of the Cl ions in the reference electrolyte 2 does not change. In state-of-the-art Ag/AgCl reference electrodes, the Cl⁻ concentration $c(CL^-)$ in the reference electrolyte is relatively constant at 3 mol/L. This applies in particular to pressurized reference electrodes, since a dilution or contamination of the reference electrode 2 can essentially be avoided with the pressurization.

The diffusion potential E2 is a function of several quantities, including the difference of the ion concentrations between reference electrolyte 2 and measurement medium 9 and the surface charge of the diaphragm 3 which is influenced by the zeta potential and the pore size of the diaphragm. The diffusion potential E2 should likewise be essentially constant and preferably have a value of 0 mV. The potentials E3 and E4 are essentially constant as long as the chloride ion potential at the second conductor element 8 and the $H^+$ ion potential of the interior electrolyte at the at the inner pH glass remain essentially constant, a condition that is satisfied due to the closed inner housing 5 with the interior electrolyte 7. The asymmetry potential E5 of a combined pH measuring chain can be considered approximately constant as long as the temperature remains constant. The potential E6 varies dependent on the $H^+$ potential at the outside of the glass membrane 6, i.e. dependent on the pH value of the measurement medium.

Figure 2:
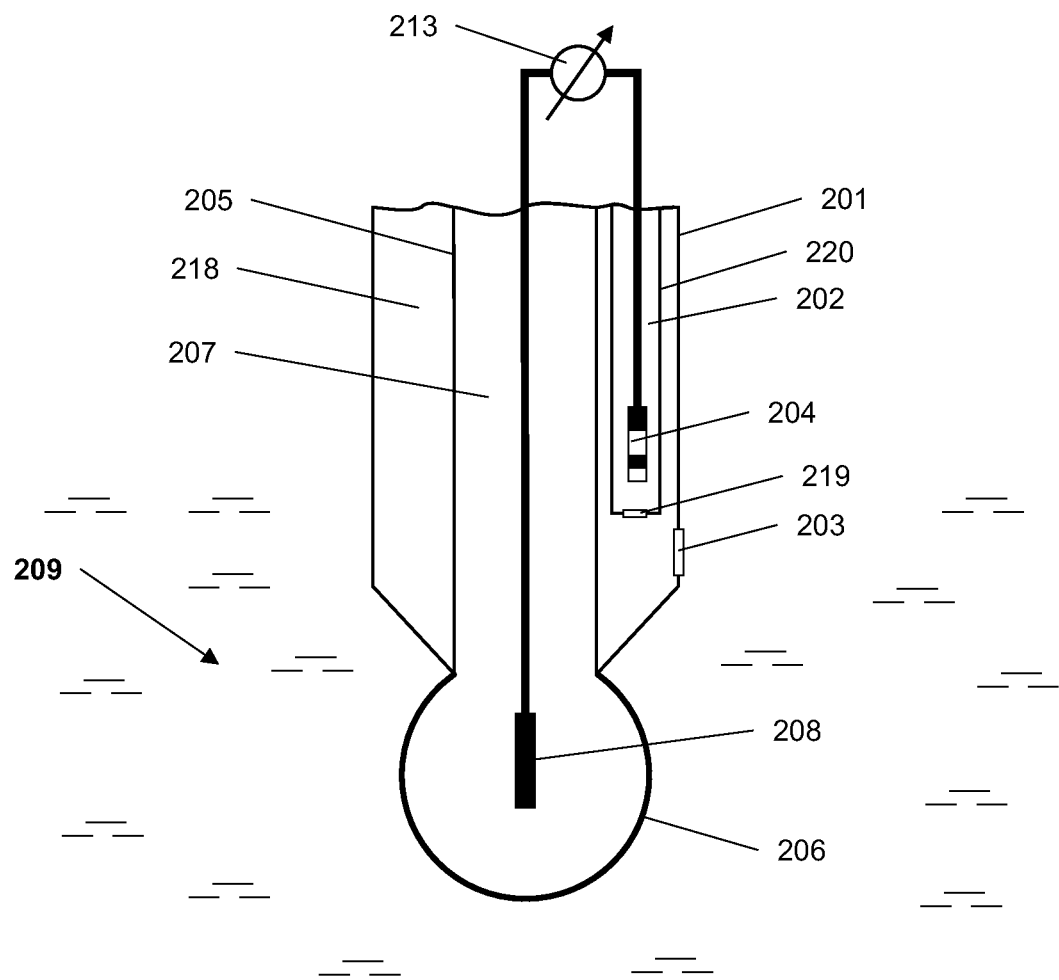
FIG. 2 schematically represents a combined pH measuring chain with a reference electrode in lengthwise sectional view, wherein the reference electrode comprises a reference electrolyte and a bridge electrolyte.

FIG. 2 illustrates a combined pH measuring chain with a dual-chamber reference system. This pH measuring chain has essentially the same characteristics as the pH measuring chain of FIG. 1, except that the pH measuring chain of FIG. 2 has a different reference electrode. The first conductor element 204 is located in a further reference housing 220 which contains the reference electrolyte 202. This reference housing 220 includes a further diaphragm 219 which represents an liquid junction between the reference electrolyte 202 and a bridge electrolyte 218 contained in the housing 201. The bridge electrolyte 218 is in contact with the measurement medium 209 by way of the diaphragm 203. The bridge electrolyte 218 represents the modifying electrolyte in the sense of the invention and includes a first component as well as a surface-modifying component, so that the diaphragm 203 is modified in situ during operation as the bridge electrolyte passes through the diaphragm.

The following examples are intended to demonstrate the influence that the addition of a surface-modifying component to the electrolyte has on a pH measurement, particularly in the case of a protein-containing measurement medium.

Figure 3:
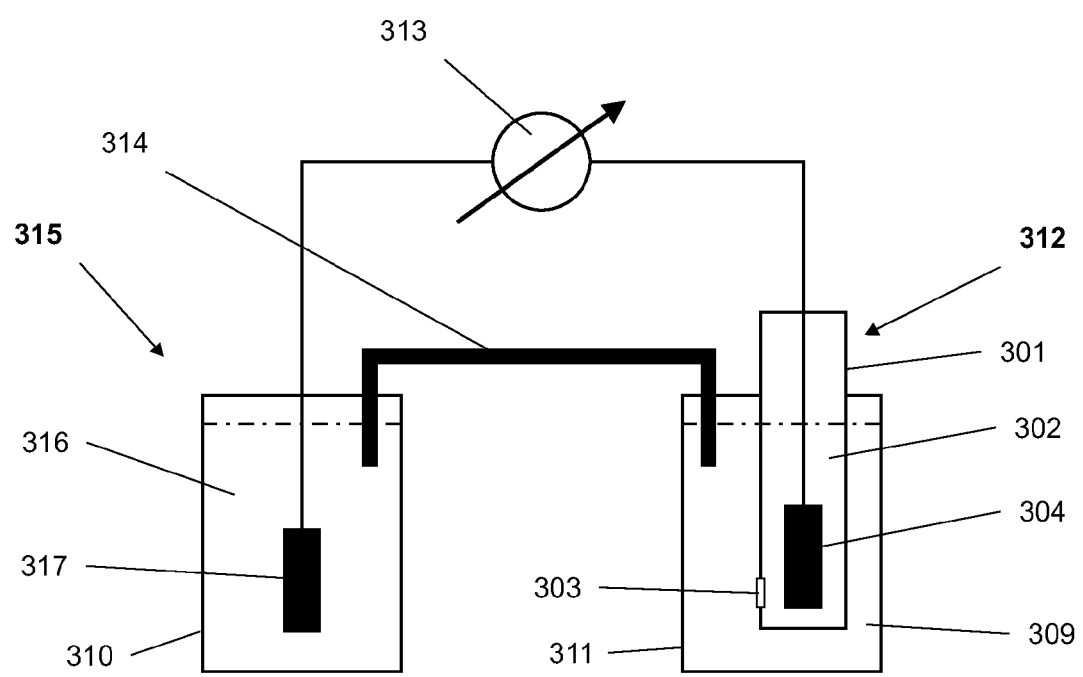
FIG. 3 schematically represents a measurement arrangement for comparison measurements of a pH reference electrode against an external reference of the same design.

In all of the examples 1 to 7, a setup according to FIG. 3 was used. The illustrated arrangement includes a pressurized reference electrode 312 which is immersed in a first container 311, and an external reference 315. The external reference 315 includes a further container 310, and the two containers 310, 311 are connected to each other through a diaphragm conduit 314. The diaphragm conduit 314 is filled with liquid and constitutes a liquid connection between the two containers 310, 311. The container 310, for example a glass beaker, contains an electrolyte 316 of the external reference 315 in which a reference element 317 is immersed. The container 310 thus constitutes the half-cell of the external reference 315.

The pressurized reference electrode 312 is immersed in a measurement medium 309 which is held by the second container 311. The reference half-cell or reference electrode 312 includes a housing 301 which is filled with a reference electrolyte 302 and has a diaphragm 301 as an interface passage to the measurement medium 309. A first conductor element 304 is again immersed in the reference electrolyte 304. The reference electrode 312 is pressurized, so that the reference electrolyte 302 can continuously flow outwards through the diaphragm 303.

In order to demonstrate how the measurement properties of a reference electrode are influenced by the addition of a surface-modifying component such as for example sodium citrate, measurements were first conducted with the arrangement according to FIG. 3 with differently configured reference electrodes 312, different compositions of the reference electrolyte 302, and different measurement media 309.

EXAMPLE 1

Standard-type Reference Electrode Against an External Reference

For the reference electrode 312, a pressurized Ag/AgCl electrode was used with an Ag/AgCl wire for the first conductor element 304 and a diaphragm 303 of microporous zirconium dioxide. The reference electrolyte 302 included only an aqueous 3 mol/L KCl solution as first component and no surface-modifying component. The reference electrode that was being used was pressurized in order to ensure a controlled migration of the reference electrolyte 302 through the diaphragm 303.

As external reference, the container 310 was used, which included an Ag/AgCl wire as second conductor element 8 and an aqueous 3 mol/L KCl solution as electrolyte 317.

The measurement medium was likewise an aqueous 3 mol/L KCl solution, and the two containers 310, 311 were connected to each other through a macroporous diaphragm tube 314.

As all electrolytes as well as the measurement medium in this example were aqueous KCl solutions of equal concentration and, consequently, no concentration gradient could establish itself through the diaphragm 303 nor through the diaphragm tube 314, the diffusion potential E2 obtained in a measurement was essentially constant at a value of zero, and therefore the sum of all potentials E1 to E6 was essentially zero.

Figure 4:
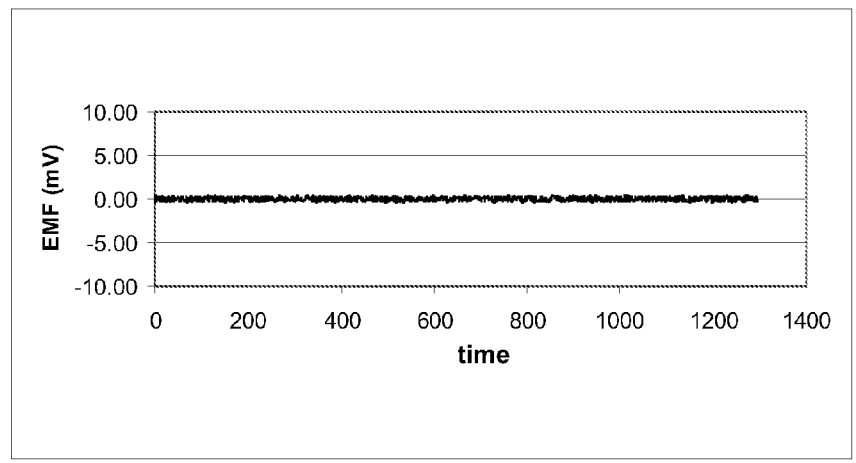
FIG. 4 shows a voltage/time diagram of an ideally performing Ag/AgCl reference electrode against an external reference of the same design, using a 3 mol/L KCl solution as the first component of the modifying electrolyte.

FIG. 4 shows a plot of the voltage vs. time diagram of the reference electrode against an external reference, which illustrates the situation just described. As can be seen in the graph, the voltage measured over time was essentially around zero.

EXAMPLE 2

Citrate-containing Measurement Medium

In a further example, which corresponds in essence to Example 1, sodium citrate in a concentration of 0.1 mol/L was added to the measurement medium 309, a 3 mol/L KCl solution, after an elapsed measurement time of 600 seconds.

These measurements were conducted with reference electrodes 312 with different pore sizes of the porous zirconium oxide diaphragm 303, specifically with average pore sizes of 70 nm, 120 nm, 200 nm, 400 nm, and 800 nm.

When sodium citrate is added to the measurement medium 309, the surface of the diaphragm is first populated with citrate ions, whereupon the surface potential (zeta potential)

and the isoelectric point (pI) of the diaphragm surface change accordingly, so that the diffusion potential E2 changes also, i.e. ceases to be constant. The change of the diffusion potential E2 is particularly pronounced in diaphragms of small pore size and in measurement media of low ion concentration and, as a result of the latter, a high level of diffusion.

Figure 5A:
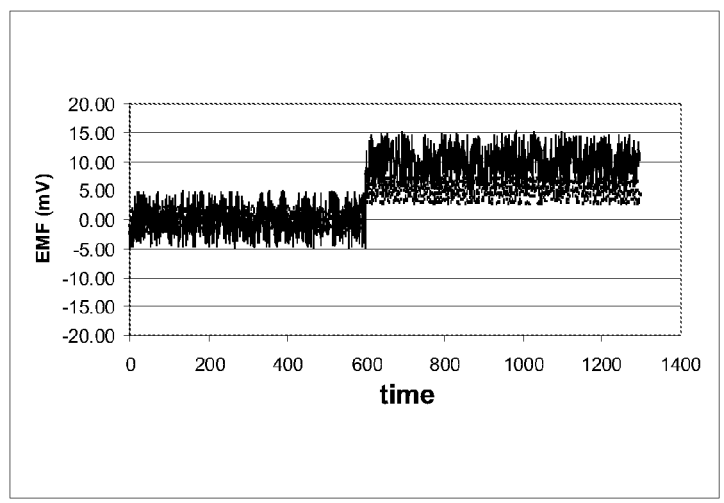
FIG. 5 shows voltage/time diagrams of an Ag/AgCl reference electrode against an external reference of the same design, wherein sodium citrate was added to the measurement medium 600 seconds after the start, and wherein the reference electrode comprises a. a zirconium dioxide diaphragm with an average pore size of 70 nm or 120 nm, b. a zirconium dioxide diaphragm with an average pore size of 200 nm, c. a zirconium dioxide diaphragm with an average pore size of 400 nm or 800 nm.
Figure 5B:
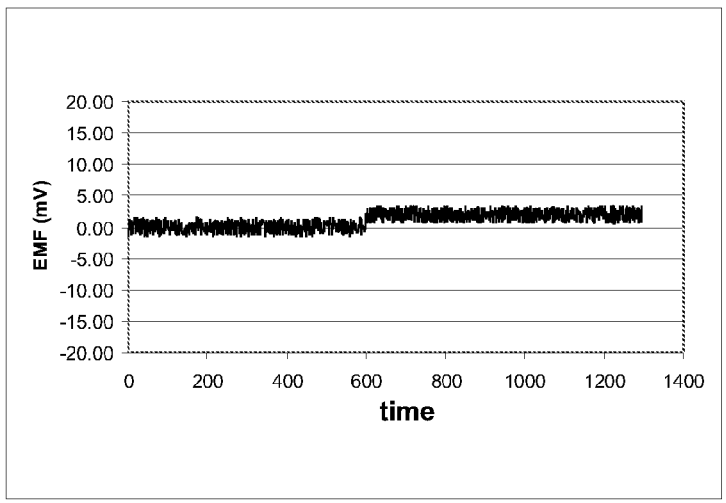
Figure 5C:
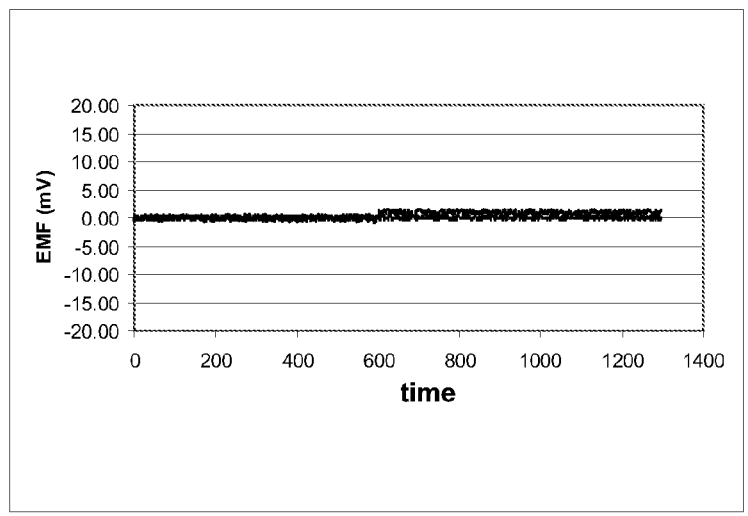

Due to the change in the potential E2, the sum of the potentials, and thus the result of the measurement, also changes, as indicated by the step change of the potential in the diagrams of FIGS. 5a to 5c, wherein the observed tendency of the diagrams is independent of the pore size of the diaphragm being used. In FIG. 5a, the solid line shows the result for a diaphragm with an average pore size of 70 nm and the broken line shows the result for a diaphragm with an average pore size of 120 nm. FIG. 2b illustrates the result for a diaphragm with an average pore size of 200 nm, and FIG. 2c for diaphragms with an average pore size of 400 nm (solid line) and 800 nm (broken line).

The effect is stronger in diaphragms of smaller pore size (FIG. 5a), due to the increased probability that an ion (including hydrate envelope) will interact with the surface of the diaphragm 303, i.e. that it will be adsorbed by the latter and/or held back in the diaphragm 303, which can result in a separation of charges and thus in a change of the diffusion potential.

In measurement media of lower ion concentration, this effect is stronger as the driving force for the diffusion increases and, accordingly, the amount of diffusion due to the difference in the respective ion concentrations of the reference electrolyte 302 and the measurement medium 309 also increases.

The higher the probability of electrolyte ions interacting with the diaphragm, the higher will be the noise lever of the measurement signal and the change in the diffusion potential E2. This probability increases with decreasing pore size of the diaphragm. The change in the diffusion potential E2 causes the step change seen in the graph at 600 sec and thus leads to a measurement error in the combined pH measuring chain.

EXAMPLE 3

Citrate-containing Reference Electrolyte

In this example, a pressurized Ag/AgCl electrode with an Ag/AgCl wire as the first conductor element 304 and a diaphragm 303 of porous zirconium dioxide were used as reference electrode 312. The reference electrolyte 302 consisted of an aqueous 3 mol/L solution of KCl as the first component, with the addition of sodium citrate in a concentration c(Na-citrate) of $5 \times 10^{-4}$ mol/L as surface-modifying component, thus enabling the reference electrolyte 302 to act as modifying electrolyte. The reference electrode used in this example was pressurized in order to ensure a controlled migration of the reference electrolyte 302 through the diaphragm 303.

The first container 310 was used as external reference electrode, containing an Ag/AgCl wire as reference element 317 and an aqueous KCl solution in a concentration of 3 mol/L as electrolyte 316.

The measurement medium was an aqueous KCl solution of 3 mol/L.

Figure 6:
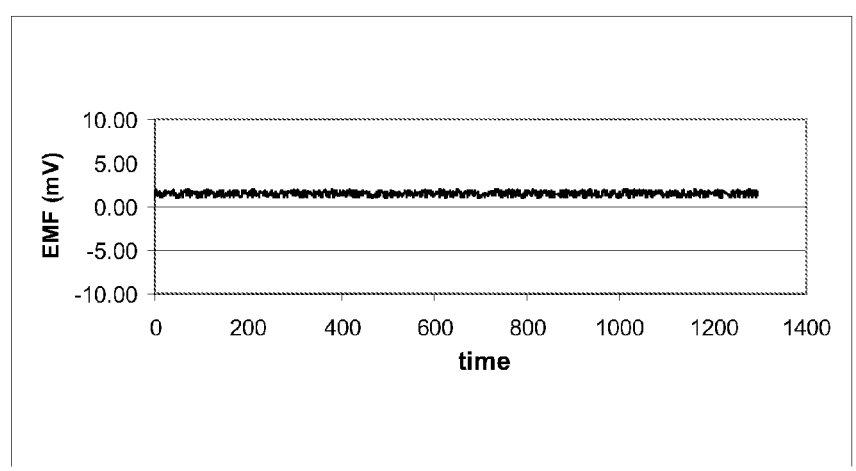
FIG. 6 shows a voltage/time diagram of an Ag/AgCl reference electrode against an external reference of the same design, wherein $5 \times 10^{-4}$ mol/L sodium citrate was added to the modifying electrolyte.

In this example the potential E2 is essentially constant, but not zero, as it is a function of the pore size of the diaphragm and this function was altered by the addition of citrate ions. Accordingly, the sum of the potentials is likewise a constant quantity, but not zero, as can be seen in the diagram of FIG. 6.

The in-situ covering or modification of the diaphragm surface by the preferably continuous outward flow of surface-modifying component, in this case sodium citrate, leads to a change in the reference potential which can be compensated, however, with a suitable calibration procedure. The shift of the zero point of the combined pH measuring chain, which can be seen in FIG. 6, can further be regulated or adjusted back to zero by adjusting the inner buffer 7.

EXAMPLE 4

Citrate-containing Reference Electrolyte and Citrate-containing Measurement Medium In this example, sodium citrate was added to the reference electrolyte 302 as well as to the measurement medium 309. In addition, at 600 sec into the measurement, sodium citrate in a concentration of 0.1 mol/L was added to the aqueous 3 mol/L KCl solution of the measurement medium 309. The further parameters of the measurement setup were the same as in Example 3, but in this case the measurements were carried out with different pore sizes of the porous zirconium oxide diaphragm 3, specifically with pore sizes of 70 nm, 120 nm, 200 nm, 400 nm, and 800 nm.

As in Example 3, the diaphragm surface was replenished with citrate ions in-situ and with preference continuously by the flow of reference electrolyte 302 which was maintained through the pressurization of the reference electrode. The diaphragm surface was therefore already occupied at the time when citrate salt was added to the measurement medium, so that the surface charge and the diffusion potentials of the diaphragm changed only to an insignificant extent.

Figure 7A:
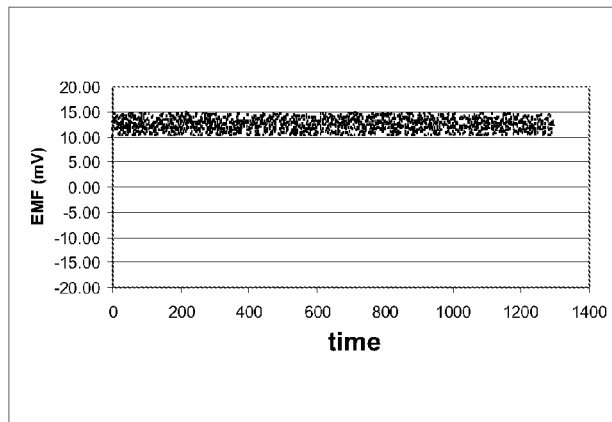
FIG. 7 shows a voltage/time diagram of an Ag/AgCl wherein $5 \times 10^{-4}$ mol/L sodium citrate was added to the modifying electrolyte, against an external reference of the same design, wherein sodium citrate was added to the measurement medium 600 seconds after the start, and wherein the reference electrode comprise a. a zirconium dioxide diaphragm with an average pore size of 70 nm or 120 nm, b. a zirconium dioxide diaphragm with an average pore size of 200 nm, c. a zirconium dioxide diaphragm with an average pore size of 400 nm or 800 nm.
Figure 7B:
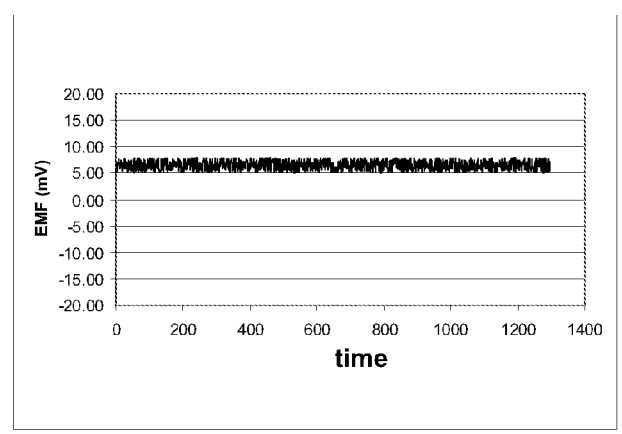
Figure 7C:
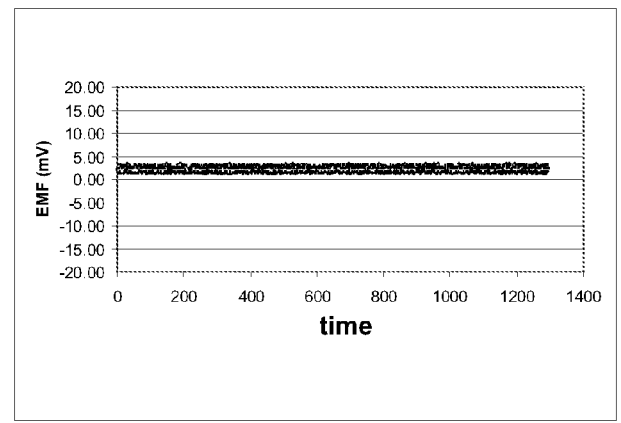

As the diagrams in FIGS. 7a to 7c illustrate, there is no longer a step increase of the potential taking place after the citrate has been added to the measurement medium. This effect is again independent of the pore sizes of the diaphragms being used. The offset of the zero point which still exists can again be compensated easily by adjusting the inner buffer. The solid line in the diagram of FIG. 7a shows the result for a diaphragm with an average pore size of 70 nm, while the broken line shows the result for a diaphragm with an average pore size of 120 nm. The result for a diaphragm with an average pore size of 200 nm is shown in FIG. 7b. In FIG. 7c, the solid line shows the result for a diaphragm with an average pore size of 400 nm, while the broken line shows the result for a diaphragm with an average pore size of 800 nm.

From Examples 1 to 4, it can be concluded that effects which interfere with the measurement result of a pH measuring chain in citrate-containing measurement media can be remedied by adding citrate salt as surface-modifying component to the reference electrolyte. It can further be concluded that even a small concentration of citrate in the modifying electrolyte, in this case the reference electrolyte, is sufficient to modify the diaphragm surface in situ and with preference continuously and to thereby counteract a further agglomeration of citrate from the measurement medium.

EXAMPLE 5

Differential Electrode with Reference Electrode According to the Invention

In a further example embodying the invention, the measurement setup according to Example 4 was adapted in that a pH reference electrode was substituted for the Ag/AgCl reference electrode. Already in the measurements of Example 4, reference electrodes with different pore sizes of the diaphragms were evaluated. For the reference electrolyte, a buffer solution of pH 4.6 was used to which ascorbic acid in a concentration of about 0.05 mol/L was added as surface-modifying component.

As already described in connection with Example 4, at about 600 seconds into the measurement, a salt of the surface-modifying component, in this case sodium ascorbate, was added to the measurement medium.

As a result of adding ascorbic acid to the reference electrolyte, in this case a pH buffer system, there was again no longer a step change appearing even after adding the ascorbate, and the effect did not depend on the pore sizes of the diaphragms being used. The still existing offset of the zero point can again be compensated easily by a change of the inner buffer.

EXAMPLE 6

Use of Metallic Structures for the Diaphragm

Analogous to the measurement setups used in Examples 1 to 4, measurement setups with metallic structures, specifically diaphragms in the form of platinum wire bundles, were also realized and tested. As a noticeable trait in the measurements that were performed, it was found that new platinum wire diaphragms had a relatively large pore size, so that reference electrodes 312 equipped with new platinum wire bundles of this kind exhibited the same effect as the reference electrodes with zirconium oxide diaphragms of large pore sizes in the examples 1 to 4.

Platinum wire bundles have the property of being very soft and a tendency to change their shape in mechanical cleaning and under mechanical stress. As result the pores in the wire bundle will become progressively smaller while the effects on the diffusion potential grow larger.

After repeated mechanical cleaning of the platinum wire bundle, for example by grinding or strong abrasion of the diaphragms, the effects on the electrical potentials of the diaphragms became larger and larger, so that in the end similar results were obtained as with the microporous diaphragms (70 nm, 120 nm) in the Examples 2 to 4.

Likewise, by using citrate-containing reference electrolytes, the effect on the diffusion potential could be reduced in a similar way as in Example 4.

From these results, the conclusion could be drawn that diaphragms with metallic structures become less susceptible to the adsorption of foreign substances, if a surface-modifying component is added to the reference electrolyte.

EXAMPLE 7

Measurement in Protein-containing Measurement Media

In the next example of an application of the method according to the invention, pH measuring chains with different reference electrodes were used to determine the pH value of a protein-containing measurement medium, and their respective measurement performances were compared to each other.

These comparative measurements were performed in a "mammalian bioprocess" for the manufacture of recombinant lactogen protein from ovarian cells of hamsters (CHO, Chinese hamster ovaries).

Proteins that are involved in this bioprocess include, among others, bovine serum albumin (BSA) with an isoelectric point around 4.5, and casein (a protein occurring in milk) with an isoelectric point around 4.6.

For the bioprocess, a 2.5 liter bioreactor with a working volume of 2 L was used (MBR Bioreactor, Zurich). The CHO cells were grown at a temperature of 35.6° C. in a reaction medium with 7 g/L glucose and 7 mmol/L glutamine as primary carbon source.

The saturation with oxygen was set at 50% and held at this level by injecting nitrogen and/or oxygen gas. The pH value of the biomass was set at pH 6.8 and held at this level by adding NaOH in a concentration of 0.3 mol/L. Next, the biomass was seeded with $8.5 \times 10^6$ CHO cells per milliliter and held constant at $10 \times 10^6$ cells/mL by continuously thinning the cells out and skimming them off. The throughput rate was about 1.5 bioreactor volumes per day, and the reactor was operated continuously over seven days.

The bioprocess was monitored with different sensors, including but not limited to oxygen sensors, temperature sensors and $CO_2$ sensors as well as several pH measuring chains of different designs. After completing seven days of cell production, the different pH measuring chains were compared to each other in regard to their measurement performance.

Following is the list of pH measuring chains tested:

|  | | Reference Electrolyte | | Diaphragm |
|---|---|---|---|---|
|  | Pressurized | KCl* | Na-citrate* | (material/average pore size) |
| PH-1 | no | 3 | — | $ZrO_x$/100 nm |
| PH-2 | yes | 3 | — | $ZrO_x$/100 nm |
| PH-3 | yes | 3 | $5 \times 10^{-4}$ | $ZrO_x$/100 nm |
| PH-4 | yes | 3 | — | Pt-wire bundle |
| PH-5 | yes | 3 | $5 \times 10^{-4}$ | Pt-wire bundle |

*The concentrations are stated in reference to pH7 and in mol/L.

Two pH measuring chains of the type PH-3 were employed, one of which was used as the process-controlling pH-measuring chain.

After completion of the 7-day bioprocess, the result in regard to the measurement performance of the different pH measuring chains was as follows.

The measuring chain PH-1 exhibited a strongly fluctuating pH-value over the course of the bioprocess and no pH-value at all at the end of the bioprocess. The pH-values indicated by the measuring chain PH-2 were affected by strong noise of up to ±1 pH units, but in contrast to PH-1, a reading of a pH-value could still be taken even after completion of the process.

The measuring chain PH-3 indicated a stable value of pH 6.8±0.1 over the course of the bioprocess.

The diaphragms of the reference electrodes of the measuring chains PH-4 and PH-5 included an old, strongly compressed platinum wire bundle and had therefore a very small pore size. The measuring chain PH-4 exhibited a behavior analogous to PH-1. The indicated pH-value fluctuated strongly, and pH-readings were no longer possible at the end of the bioprocess. The measuring chain PH-5 showed, like PH-3, the correct value of pH 6.8, albeit with a somewhat higher amount of noise of 0.2 pH units.

After completion of the bioprocess, all five pH measuring chains were calibrated at pH 4 and pH 7 with standard buffer solutions In the calibration process it was found that the measuring chains PH-1 and PH-4 could not be calibrated as no end values were available due to excessive noise.

The calibration of the measuring chain PH-2 could still just be performed, albeit only after long waiting periods, as the response of the measuring chain PH-2 was strongly slowed down. It was found that the steepness of the characteristic of the measuring chain PH-2 had deteriorated and that the latter, in particular due to the slow response and/or the very noisy signals, indicated no sufficiently stable end values.

It was tried to regenerate the measuring chains PH-1, PH-2 and PH-4 and to perform another calibration. To accomplish this, the measuring chains were regenerated over 12 hours in a regeneration solution of hydrochloric acid and pepsin (Mettler-Toledo) and calibrated again in buffer solutions of pH 4 and pH 7.

The measuring chain PH-2 could be regenerated and subsequently calibrated again in this manner. After this procedure, the zero point of the measuring chain PH-2 was at 5 mV with a steepness of 97.6%.

After the regeneration, the measurement values of the measuring chains PH-1 and PH-4 still exhibited a high noise level of ±5 mV in the calibration with the buffer solution of pH 4 and took a long time to establish a measurement value. After the change to the pH 7 buffer, the measurement values again turned out to be very noisy and no end value could be determined.

Obviously, even a regeneration of the measuring chain over twelve hours in HCl/pepsin was not enough to completely remove the protein absorption at the surface of the diaphragm.

Thus, even after twelve hours of regeneration the measuring chains PH-1 and PH-4 achieved neither an adequate measurement performance nor a sufficient reproducibility in protein-containing measurement media and could therefore no longer be used for further measurements.

Although the measurement chain PH-2 could be regenerated, its measurement performance in protein-containing solutions was clearly diminished.

In contrast, the measuring chains PH-3 and PH-5 which, in accordance with the invention, had a reference electrode with a modifying electrolyte exhibited a very good calibration behavior and settled quickly on stable end values. Even after seven days of operation in a bioprocess with a high protein content, the measurement chains still showed steepness values of 98% (PH-3) and 96.3% (PH-4), respectively.

Although the invention has been described by presenting specific examples of embodiments, it is considered self-evident that numerous further variants could be created based on the teachings of the present invention, for example by combining the features of the individual embodiments with each other and/or interchanging individual functional units between the embodiments.

What is claimed is:

1. A method for the in-situ modification of a porous diaphragm which is arranged in a reference electrode as a liquid connection to a measurement medium, the reference electrode comprising at least one housing, a first conductor element, a modifying electrolyte, comprising a first component and arranged in one of the at least one housings as a free-flowing liquid, and the porous diaphragm, which establishes a liquid connection between the housing containing the modifying electrolyte and the measurement medium and through which the modifying electrolyte seeps out during operation, and a reference electrolyte, contained in a reference housing that has a further porous diaphragm, the first conductor element being immersed in the reference electrolyte, which is in contact with the modifying electrolyte, which serves as a bridge electrolyte by way of the further porous diaphragm, wherein the method comprises the steps of:
adding a surface-modifying component to the modifying electrolyte that is arranged in the reference electrode, wherein the surface-modifying component modifies a surface of the porous diaphragm in situ during the passage of the modifying electrolyte, and
ensuring the outward migration of the modifying electrolyte through the porous diaphragm.

2. The method according to claim 1, wherein:
the modifying electrolyte continuously exits through the porous diaphragm during operation.

3. A reference electrode for contact with a measurement medium, comprising:
at least one housing;
a first conductor element;
a modifying electrolyte, comprising a first component and a surface-modifying component, the modifying electrolyte being a free-flowing liquid that is arranged in one of the at least one housings to provide a bridge electrolyte; and
a porous diaphragm which establishes a liquid connection between the housing containing the modifying electrolyte and the measurement medium and through which the modifying electrolyte seeps out during operation, wherein the surface-modifying component modifies the surface of the porous diaphragm in situ during the passage of the modifying electrolyte; and a reference electrolyte, contained in a reference housing that has a further porous diaphragm, the first conductor element being immersed in the reference electrolyte, which is in contact with the modifying electrolyte, which serves as a bridge electrolyte by way of the further porous diaphragm.

4. The reference electrode according to claim 3, wherein:
the surface of the porous diaphragm is modified continuously.

5. The reference electrode according to claim 3, wherein:
the reference electrode is pressurized so that, during operation, the modifying electrolyte continuously seeps out through the porous diaphragm.

6. The reference electrode according to claim 3, wherein:
the modifying electrolyte is a reference electrolyte in which the first conductor element is immersed.

7. The reference electrode according to claim 3, wherein:
the surface-modifying component comprises an electrostatically-acting substance.

8. The reference electrode according to claim 3, wherein:
the surface-modifying component comprises a sterically demanding substance.

9. The reference electrode according to claim 3, wherein:
the surface-modifying component comprises an organic substance having at least one hydroxy substituent and at least one carbonyl substituent.

10. The reference electrode according to 9, characterized in that the surface-modifying component is selected from the group consisting of: lactic acid, citric acid, malic acid, tartaric acid, ascorbic acid, salts of said acids, and mixtures thereof.

11. The reference electrode according to claim 9, wherein:
the surface-modifying component comprises polylysine polyethylene glycol.

12. The reference electrode according to claim 3, wherein:
the surface-modifying component Is present in the modifying electrolyte in a concentration of less than 0.1 weight percent, in particular from about 0.05 to 0.1 weight percent.

13. The reference electrode according to claim 3, characterized in that the porous diaphragm comprises a ceramic material.

14. The reference electrode according to claim 3, wherein:
the porous diaphragm comprises a metallic structure.

* * * * *